(12) United States Patent
Pesu et al.

(10) Patent No.: US 6,391,398 B1
(45) Date of Patent: May 21, 2002

(54) FRAGRANT ARTIFICIAL FLOWER APPARATUS

(75) Inventors: Maxine Pesu; Kathy LaVanier, both of Reynoldsburg, OH (US); Kenneth W. Lesenko, Clifton, NJ (US)

(73) Assignee: Bath & Body Works, Inc., Reynoldsburg, OH (US)

( * ) Notice: Subject to any disclaimer, the term of this patent is extended or adjusted under 35 U.S.C. 154(b) by 0 days.

(21) Appl. No.: 09/551,020

(22) Filed: Apr. 18, 2000

(51) Int. Cl.$^7$ .................................................. A47G 1/12

(52) U.S. Cl. ......................... 428/13; 428/24; 428/34.1; 428/542.8; 428/905

(58) Field of Search ........................... 428/24, 25, 34.1, 428/542.8, 403, 905, 13; 47/41.12, 41.13; 239/55, 53, 47, 60, 51.5; 424/76.3; D23/366

(56) References Cited

U.S. PATENT DOCUMENTS

| 2,807,901 A | * | 10/1957 | Gilowitz |
| 3,400,890 A | * | 9/1968 | Gould |
| 4,919,981 A | * | 4/1990 | Levey et al. .................. 428/26 |
| 5,353,546 A | * | 10/1994 | Bock .............................. 47/66 |
| 5,687,502 A | * | 11/1997 | Weder ....................... 47/41.01 |

\* cited by examiner

*Primary Examiner*—Blaine Copenheaver
*Assistant Examiner*—Abraham Bahta
(74) *Attorney, Agent, or Firm*—Colucci & Umans; Peter C. Michalos; Angelo Notaro

(57) ABSTRACT

An artificial fragrance emitting flower article has at least one artificial flower having a stem. A vessel has an open top defined by a rim and an interior chamber defined by an inside surface of the vessel. A base having a top surface is mounted within the interior chamber of the vessel. The stem of the artificial flower is partially encased in the base. A fragrant gel layer is positioned on the top surface of the base to emit fragrance through the open top of the vessel.

8 Claims, 1 Drawing Sheet

FRAGRANT ARTIFICIAL FLOWER APPARATUS

FIELD AND BACKGROUND OF THE INVENTION

The present invention relates generally to the field of air fresheners, and in particular, to a fragrant artificial flower apparatus. The invention concerns a novel self-contained air freshener which provides an artificial air freshening fragrance in combination with the beauty of an artificial flower display.

Flowers have both aromatic and visual mood enhancing properties. A bouquet of flowers will enhance the atmosphere of an entire room. However, for a variety of reasons, the indoor display of living flowers is limited.

First, living flowers, and particularly valuable ornamental flowers, require care if they are to be kept alive. There are thus two options--buying expensive cut flowers with the understanding that they are to be disposed of in a matter of days, or buying potted flowers with the understanding that they must require years of care. Potted flowers are bulky, and many people do not have the time or talent to care for living flowers.

Accordingly, in view of the problems associated with living plants, many people have settled on imitation flowers which require little or no care.

Devices have been developed which combine the functions of floral display and artificial fragrance dispenser. For example, U.S. Pat. No. 5,353,546 to Bock teaches a combination vase and air fragrance dispenser comprising two vessels, one for holding natural or artificial flowers, the other for holding a fragrance emitting material. The two-vessel construction ensures complete separation between flower and air treatment material, preventing contamination of the flowers. The flower holding vessel is capable of receiving water needed to keep natural flowers fresh. Thus, this device is concerned with the display of cut flowers, which have a short life.

U.S. Pat. No. 5,477,640 to Holtkamp, Jr. teaches a fragrance emitting plant watering system, wherein a potted natural flowering plant is seated within a larger vase-like solid fragrance emitter. A wick transports water from a water reservoir to a potted plant. An air freshener cartridge for emitting a fragrance is provided in a separate compartment of the device. The device however greatly and unnecessarily increases the size of the vase and provides a proportionately small space in which to place the potted flowering plant. This renders the device unsuitable for display in areas where space is limited, such as in office cubicles. The device is also uneconomical due to the expense of manufacturing such a complex device.

U.S. Pat. No. 5,081,104 to Orson discloses an air fragrance dispenser including a reservoir of a volatile fragrance solution, a diffuser surface from which the fragrance is dispersed into the air, a wick for transporting the fragrance from the reservoir to the diffuser by capillary action, and a particular chemical composition for regulating the fragrance evaporation rate.

U.S. Pat. No. 5,077,102 to Chong discloses a scented artificial flower with a stem that extends from the ovary of the flower into a reservoir of perfume. A wick within the stem connects the perfume reservoir to the ovary and stamen elements of the flower, which are both constructed of a wicking material. The perfume may be supplied to the ovary and stamens by capillary action or pressure supplied by a pump. Alternatively, the stem may be a hollow tube that supplies the perfume to the ovary and stamens by gravity, from an elevated container.

U.S. Pat. No. 4,958,768 to Ishihara discloses an artificial potted flower wherein deodorant and/or perfume is entrapped in swollen gels of water-absorbent synthetic resin and released by the moisture-releasing property of water-absorbent resin in the case of a deodorant, or by inherent sublimability in the case of a perfume.

U.S. Pat. No. 4,928,881 to Barlics discloses a conventional air freshener, shaped to resemble a flower. The air freshener includes a wick in communication with a liquid reservoir. The wick is formed by a bundle of strands of polyester or other suitable material capable of carrying the liquid by capillary action from the reservoir to a diffusing site. The wick directly disperses the air freshener to the air at the diffusing site without the intervention of a separate scent pad.

U.S. Pat. No. 4,919,981 to Leavey, et. al. discloses an air freshener in the form of a decorative vase containing one or more artificial flowers. A stem-like wick extends between a reservoir of liquid air freshener within the vase, and a vapor dispenser. The vapor dispenser may take the form of flat leaf-like pad elements or sponge-like elements formed and colored to resemble an artificial flower or a portion thereof. The reservoir may be partitioned into a number of sections each capable of containing a liquid having a different scent.

A fragrant artificial flower having a perfume reservoir supported with the flower's sepal is disclosed in U.S. Pat. No. 3,861,991 to Kim. The artificial flower's stamens and pistil function as wicks by extending into the perfume reservoir to absorb and release the perfume into the air.

U.S. Pat. No. 3,400,890 to Gould discloses an artificial flower or potted plant having a component formed from an absorbent hydrogel capable of absorbing and storing the solids in a fragrant essence solution. The hydrogel releases the fragrance to the air when it is exposed to an appropriate solvent. The hydrogel may be present in a portion of the flower, with the solvent supplied to this part of the flower through a wick in communication with a solvent reservoir.

U.S. Pat. No. 2,807,901 to Gilowitz et al. is for an artificial flower display enclosed in a transparent globe. A tube container filled with liquid perfume extends upwardly within and through the top center of the globe. A wick in the tube container absorbs and releases the perfume at the top of the globe.

U.S. Pat. No. 2,577,320 to Fenyo is directed to a three dimensional flower display composed of sheets of Lucite which are stacked but spaced from one another and mounted within a frame. Flower parts are arranged on each Lucite sheet so that when the Lucite sheets are mounted, the flower parts overlap and produce a three-dimensional flower display. The frame has a recess along one of its edges that contains a perfume saturated wick. The wick is covered by a hinged plate having holes for releasing fragrance.

A need remains for a simple and economical artificial floral arrangement that dispenses fragrance and that has the appearance of a decorative flower, and which avoids the complexity and expense of the prior art.

SUMMARY OF THE INVENTION

While the above described aromatic substance dispensers provide convenient means for fragrancing an area, they do not disclose the unique artificial flower apparatus and fragrance delivery system of the instant invention. Accordingly, there is a need for a combination artificial flower display and fragrance emitter which is inexpensive, attractive, relatively small in size, and easy to maintain.

Accordingly, the primary object of the invention is to provide an economical, controlled fragrance dispenser.

An object of this invention is to provide a simple, inexpensive means for producing a desirable scent or fragrance from an artificial floral display.

Another object of this invention is to provide an inexpensive article for use with a bunch of artificial flowers to produce a desirable scent or fragrance when desired and for as long as desired.

It is an object of this invention to provide a new and novel arrangement for providing floral scents for artificial plants and flowers while maintaining a natural appearance.

Yet another object of this invention is to provide a simple means for producing a fragrance emitting artificial flower-type article utilizing inexpensive and readily available materials without any substantial increase in the labor in making the article.

An additional object of the invention is to provide a passive fragrance dispenser which does not make use of a liquid reservoir.

Accordingly, an artificial fragrance emitting flower article is provided comprising at least one artificial flower having a stem; a vessel having an open top defined by a rim, the vessel having an interior chamber defined by an inside surface of the vessel; a base mounted within the interior chamber of the vessel, the base having a top surface, the stem of the artificial flower being partially encased in the base; and a fragrant gel layer positioned on the top surface of the base to emit fragrance through the open top of the vessel.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

The present invention provides an air freshener which offers both an attractive artificial flower display and an air freshening fragrance.

Figure 1:
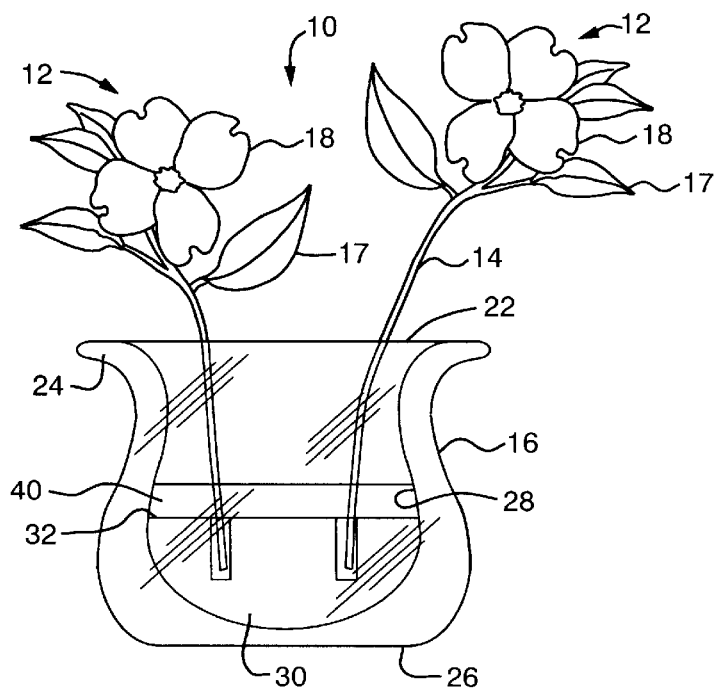
FIG. 1 is a front elevational view of the artificial fragrance emitting flower apparatus of the present invention.

Referring now to the drawings, in which like reference numerals are used to refer to the same or similar elements, FIG. 1 shows a front elevational view of the artificial flower display 10 having flowers 12 arranged in a vessel 16. The artificial flowers 12 are conventional. The construction of the flowers 12 may vary. In general, each flower 12 comprises a stem 14, leaves 17 and flowers 18 and/or other botanical parts. These flower parts may be formed of silk, polyester/cotton, polyester, pongee, taffeta, plastic material, paper materials or other types of conventional sheet materials that are used in the construction of artificial flowers.

Vessel 16 has an open top 22 defined by a rim 24, an interior chamber 26 defined by the inside surface 28 of the vessel 16 and a bottom 26. Vessel 16 is transparent.

A base 30 having a top surface 32 is contained within the vessel 16. Stem 14 of each artificial flower 12 is partially encased in base 30. Base 30 is preferably adapted to conform to the inside surface of vessel 16.

Base 30 and vessel 16 are preferably transparent so that stems 14 may be seen though the transparent vessel 16.

Base 30 can be formed of Lucite (a DuPont trademark for an acrylic resin) or bisphenol A/Epichlorohydrin resin (Silpak, Inc., Pomona, Calif.) or other transparent materials sufficient to support and encase stems 14 of flowers 12. A preferable composition of the base is amine resin (40–55% weight) and a curing agent (55–45% weight).

Vessel 16 may have a different shapes, including rectangle, circular, octagonal, oval and square.

When the gel layer 40 no longer gives off fragrance, the old gel layer can be removed and a new layer can be poured onto base 30.

Figure 2:
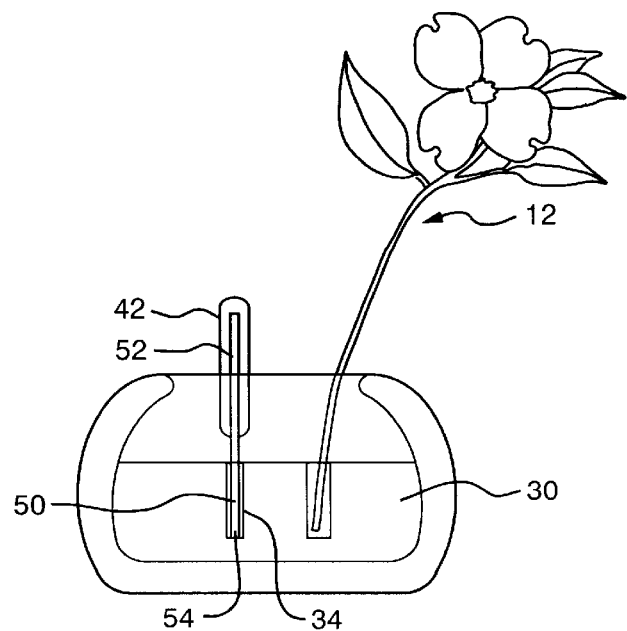
FIG. 2 is a front elevational view of an another embodiment of the present invention.

Referring to FIG. 2, in another embodiment of the present invention, rods 50 have one end 52 which holds fragrant gel 42 and an opposite end 54 that is received in a bore 34 located in base 30. Rods 50 are placed among artificial flowers 12 and are preferably removable from base 30. Rods 50 may be formed of wood, Lucite, plastic, such as PET or styrene, or any hard material and are preferably green color to allow for blending with the color aura of flowers 12 or clear so they cannot be seen.

The fragrance gel held on rods 50 is preferably composed of Isopar M (83.70% weight) available from Exxon Chemical, Kraton G1650 (8.00% weight) available Shell Chemical Co., gelling agent GP-1 (0.30% weight) available from Ajinomoto Co. Inc. and fragrance oil (8.00% weight) available from Haarmann & Reimer.

To use the embodiment of FIG. 2, one dips the top end 52 of rod 50 into a container of the gel 42. The gel 42 forms a layer on the stick and the bottom end 54 is slipped into hole 34. When the 42 gel is used up, the rod 50 can be redipped.

A coloring agent may be added to the gel composition to allow the gel 42 to match the color of the flowers 12. A preferable coloring agent is Phosphorescent Pigment 2330 M2330 available from USR Optonix Inc.

A specific embodiment of the invention has been shown and described in detail to illustrate the application of the principles of the invention, it will be understood that the invention may be embodied otherwise without departing from such principles.

What is claimed is:

1. A decorative and fragrant apparatus comprising:
   a rigid base having at least one bore;
   at least one simulated flower having a stem extending into the base for supporting the flower in an upright position over the base;
   at least one rod having one end for holding a fragrant gel and an opposite end received in the at least one bore in the base to support the gel over the base and among the at least one simulated flower.

2. The decorative and fragrant apparatus as claimed in claim 1, wherein the base is composed of an acrylic resin.

3. The decorative and fragrant apparatus as claimed in claim 1, wherein the base is transparent.

4. The decorative and fragrant apparatus as claimed in claim 1, wherein the rod is composed of wood.

5. The decorative and fragrant apparatus as claimed in claim 1, wherein the rod is composed of a clear plastic.

6. A decorative and fragrant apparatus comprising:

a rigid base having a top surface;

at least one simulated flower having a stem at least partially encased in the base for supporting the flower in an upright position over the base; and at least one rod having one end for holding a fragrant gel and an opposite end received in a bore in the base to support the gel over the base and among the at least one simulated flower, the fragrant gel dispersing a fragrance.

7. The apparatus of claim 6, wherein the at least one rod is composed of wood.

8. The apparatus of claim 6, wherein the at least one rod is composed of a clear plastic.

* * * * *